United States Patent [19]

Podszun et al.

[11] Patent Number: 5,486,548
[45] Date of Patent: Jan. 23, 1996

[54] ACRYLATES AND METHACRYLATES BASED ON CYCLOHEXYLDIPHENOLS

[75] Inventors: Wolfgang Podszun, Köln, Germany; Michael Müller, Mortsel, Belgium

[73] Assignee: Bayer Aktiengesellschaft, Leverkusen, Germany

[21] Appl. No.: 275,211

[22] Filed: Jul. 14, 1994

[30] Foreign Application Priority Data

Jul. 21, 1993 [DE] Germany ............... 43 24 431.9

[51] Int. Cl.$^6$ ............... C08F 20/30; C08F 20/20; A61C 13/087; A61K 6/083
[52] U.S. Cl. ............... 523/115; 523/116; 523/120; 524/559; 526/323.1; 526/326; 433/212.1
[58] Field of Search ............... 523/115, 116, 523/120; 524/559; 526/323.1, 326; 433/212.1

[56] References Cited

U.S. PATENT DOCUMENTS

| | | | |
|---|---|---|---|
| 4,017,454 | 4/1977 | Müller | 523/117 |
| 4,323,348 | 4/1932 | Schmitz-Josten et al. | 523/116 |
| 4,323,696 | 4/1982 | Schmitz-Josten et al. | 526/220 |

FOREIGN PATENT DOCUMENTS

| | | |
|---|---|---|
| 2347591 | 4/1975 | Germany. |
| 3135115 | 3/1983 | Germany. |
| 4136488 | 5/1993 | Germany. |

OTHER PUBLICATIONS

Chemical Abstracts, vol. 110, No. 18, May 1, 1989.
Am. Chem. Soc. Symp. Ser., 212, (1983), 359–371, G. M. Brauer, et al.
Gachter, Muller "Taschenbuch der Kunststoff–Additive", pp. 133–232, (1989).
Ullmanns Encyclopadie der technischen Chemie, 4th Ed., vol. 8, pp. 19–45, (1974).
Plueddemann et al. *Progress in Organic Coatings*, 11, pp. 297–308 (1983).
Chemical Abstract, vol. 119, 1993, p. 842 (Preparation of dialkenyl compounds as reactive diluents for oxidative cross–linking of alkyd resins.).

Primary Examiner—Paul R. Michl
Assistant Examiner—Andrew E. C. Merriam
Attorney, Agent, or Firm—Sprung Horn Kramer & Woods

[57] ABSTRACT

The invention relates to diacrylates and dimethacrylates which are derived from cyclohexyldiphenols.

Di(meth)acrylates are used widely, for example, as a component of plastic filling materials in dental engineering.

4 Claims, No Drawings

ACRYLATES AND METHACRYLATES BASED ON CYCLOHEXYLDIPHENOLS

The invention relates to diacrylates and dimethacrylates which are derived from cyclohexyldiphenols.

Di(meth) acrylates are used widely, for example, as a component of plastic filling materials in dental engineering.

A particularly frequently used monomer is the so-called BisGMA, of the formula (I)

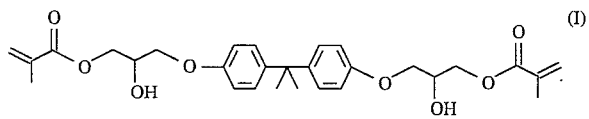

BisGMA-based materials have a favourable level in terms of mechanical properties, but they absorb water to a considerable extent, which is undesired for some purposes, for example in the case of plastic fillings.

DE-A-4,136,488 discloses monomers of the formula (IIb), where n=0 which are suitable as reactive diluents for oxidatively crosslinking alkyd resins in the technology of surface coatings.

New monomers which, in the cured state, absorb little water and have a higher glass transition temperature, have been found. Another advantage of most of the monomers according to the invention is their viscosity, which is low in comparison with BisGMA, so that these monomers can be used together with a reduced amount of reactive diluent or in the complete absence of reactive diluent.

The invention relates to monomers of the formula (IIa)

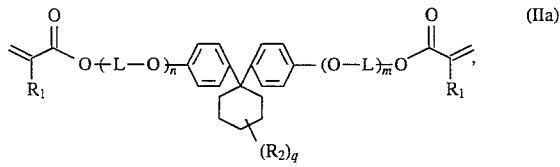

in which $R_1$ represents hydrogen or methyl,

L represents a $C_2$- to $C_6$-alkylene radical which can be substituted by alkyl, hydroxyl or halogen, $R_2$ represents a $C_1$- to $C_{12}$-alkyl radical, preferably a methyl radical, n and m independently of one another denote an integer from 1 to 4 and q represents an integer from 0 to 6.

Preferred monomers are those of the formula (IIIa)

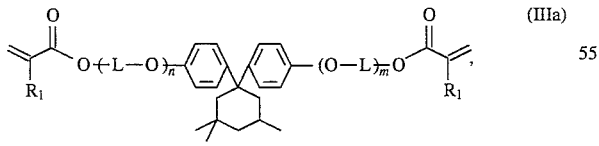

in which $R_1$, L, n and m have the abovementioned meaning.

Preferred examples of L are ethylene, 1,2-propylene and 2-hydroxy-1,3-propylene. n and m independently of one another can denote integers between 1 and 4, 1 or 2 is preferred, 1 is particularly preferred.

The present invention also relates to the use of monomers of the formula (IIb)

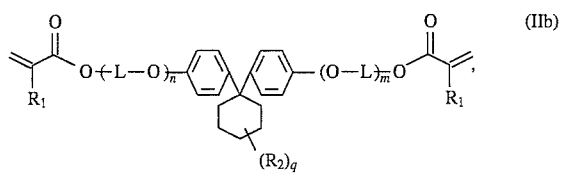

in which $R_1$ represents hydrogen or methyl,

L represents a $C_2$- to $C_6$-alkylene radical which can be substituted by alkyl, hydroxyl or halogen, $R_2$ represents a $C_1$- to $C_{12}$-alkyl radical, preferably a methyl radical, n and m independently of one another denote an integer from 0 to 4 and q denotes an integer from 0 to 6, in dental engineering, in particular in the preparation of plastics for use in dental technology, for example plastic filling materials and artificial teeth, and the resulting dental objects themselves.

Monomers of the formula (IIIb)

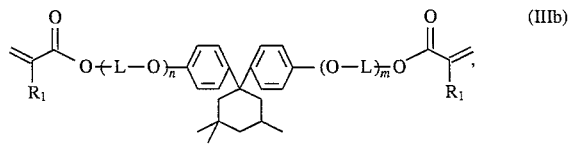

in which $R_1$, L, n and m have the abovementioned meaning, are preferably used.

Preferred examples of L are ethylene, 1,2-propylene and 2-hydroxy-1,3-propylene. n and m preferably denote 1 or 2, particularly preferably 1.

The reason why monomers of the formula (IIIa) are a preferred embodiment of the invention and why monomers (IIIb) are preferably used is because the monomers where n, m≧1 display a reduced tendency to crystallize.

The following monomers which can be used according to the invention may be mentioned by way of example:

Monomer 1

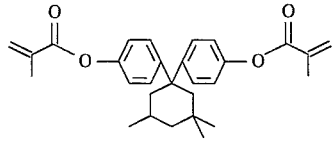

Monomer 2

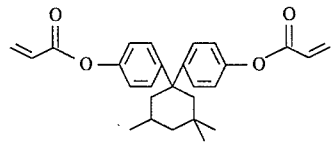

Monomer 3

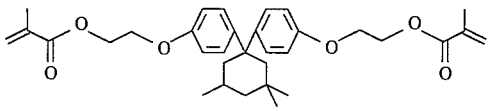

Monomer 4

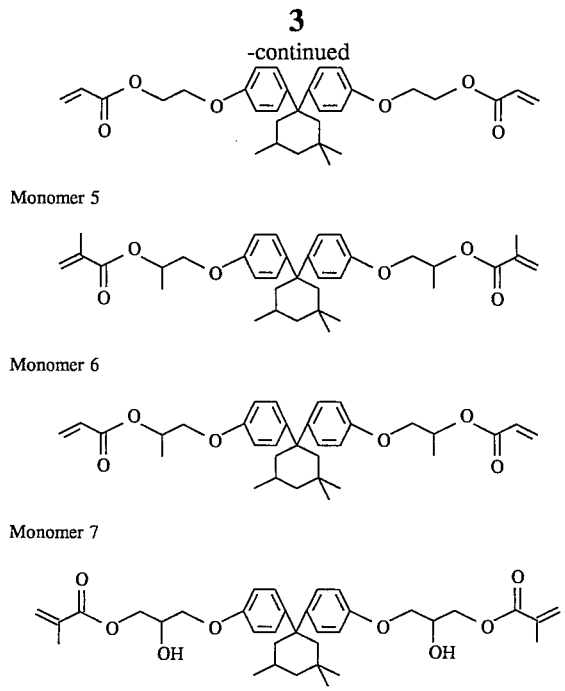

Monomer 5

Monomer 6

Monomer 7

The monomers according to the invention are expediently prepared with the bisphenols on which they are based. Monomers of the type of monomers 1 and 2 are accessible by esterification using (meth) acrylic acid or (meth)acrylic anhydride or by transesterification using (meth)acrylates of short-chain alcohols having 1 to 4 C atoms in the alcohol moiety (cf. also DE-A-4,136,488). The esterification using (meth) acryloyl chloride is preferred. In the synthesis of monomers of the type of monomers 3 to 6, bisphenol is first reacted with the desired amount of ethylene oxide or propylene oxide, with alkaline catalysis, and the product is subsequently esterified. Monomers of the type of monomer 7 can be synthesized in accordance with the following diagram:

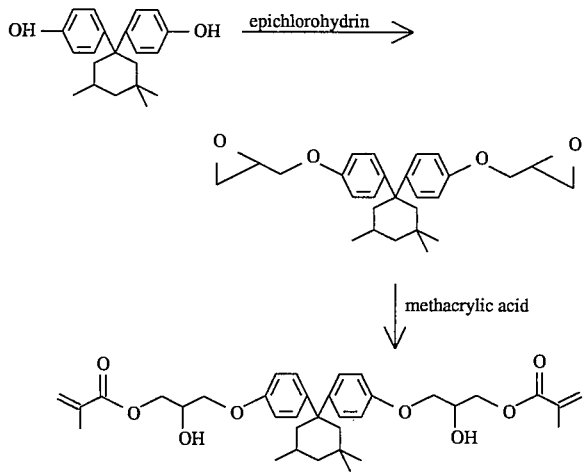

The (meth)acrylates of the formulae (IIb) and (IIIb) can also be employed as monomeric component for polymerizable tooth-filling compositions.

For this use as monomers for polymerizable tooth-filling compositions in the dental sector, the (meth)acrylates according to the invention can be mixed with monomers which are known per se, for example to adapt the viscosity to suit the intended purpose. Viscosities in the range from 60 to 10,000 mPa.s are preferred. This can be achieved, if appropriate, by admixing a low-viscosity comonomer with the monomers according to the invention to act as reactive diluents or solvents. The compounds according to the invention are employed in the mixture with comonomers in an amount of approximately 30 to approximately 100% by weight, preferably 40 to 80% by weight.

The following comonomers may be mentioned by way of example: glycerol dimethacrylate, triethylene glycol dimethacrylate, tetraethylene glycol dimethacrylate, 1,12 -dodecanediol dimethacrylate, 1,6 -hexanediol dimethacrylate, diethylene glycol dimethacrylate, 2,2-bis-(p-(2'-hydroxy-3'-methacryloyloxypropoxy)phenyl)-propane, 2,2-bis-(p-(2'-methacryloyloxyethoxy)phenyl)-propane, trimethylol-propane-tri-(meth)acrylate, bis-(meth)-acryloyloxyethoxymethyl-tricyclo-(5,2,1,0$^{2,6}$)-decane (German Offenlegungsschrift 2,931,925 and German Offenlegungsschrift 2,931,926).

Comonomers which have a boiling point of above 100° C. at 13 mbar are particularly preferred.

The (meth)acrylates according to the invention, if appropriate in a mixture with the abovementioned comonomers, can be cured by methods known per se to give crosslinked polymers (Am. Chem. Soc., Symp. Ser. 212, 359–371 (1983)). Suitable for the so-called redox polymerization is a system composed of a peroxide compound and a reducing agent, for example based on tertiary aromatic amines. Examples of peroxides are: dibenzoyl peroxide, dilauroyl peroxide and di-4-chlorobenzoyl peroxide.

Examples of tertiary aromatic amines which may be mentioned are N,N-dimethyl-p-toluidine, bis-(2-hydroxyethyl)-p-toluidine, bis-(2-hydroxyethyl)- 3,5-dimethylaniline and N-methyl-N-(2-methylcarbamoyloxypropyl)-3,5-dimethylaniline. The concentration of the peroxide or the amine are advantageously selected in such a way that they are 0.1 to 5% by weight, preferably 0.5 to 3% by weight, based on the monomer mixture.

The peroxide- or amine-containing monomer mixtures are stored separately until used.

The monomers according to the invention can also be polymerized by irradiation with UV light or visible light (for example in a wavelength range of 230 to 650 nm). Suitable initiators for the photoinitiated polymerization are, for example, benzil, benzil dimethyl ketal, benzoin monoalkyl ether, benzophenone, p-methoxybenzophenone, fluorenone, thioxanthone, phenanthrenequinone and 2,3-bornanedione (camphor quinone), if appropriate in the presence of synergistically acting activators, such as N,N-dimethylaminoethylmethacrylate, triethanolamine or N,N-diallyl-4-(N,N-dimethylamino)benzenesulphonamide. The way in which the photopolymerization is carried out is described, for example, in German Patent Specification 3,135,115.

Other substances which can be added to the (meth) acrylic acid derivatives according to the invention, besides the above-described initiators, are stabilizers and light stabilizers which are known per se for this purpose.

Light stabilizers are described, for example, in "Gächter, Müller, Taschenbuch der Kunststoff-Additive (Plastic Additives Compendium), 2nd Edition, Carl Hanser Verlag". The following light stabilizers may be mentioned by way of example: Cyasorb UV 9®, Tinuvin P®, Tinuvin 770®, Tinuvin 622®, Tinuvin 765®.

Stabilizers are described, for example, in "Ullmanns Encyclopädie der techischen Chemie (Ullmann's Encyclopaedia of Industrial Chemistry), 4th Edition, Volume 8". The following stabilizers may be mentioned by way of example: 2,6-di-tert-butylphenol, 2,6-di-tert-butyl- 4-methylphenol, 2,6-di-octadecyl-4-methyl-phenol, 1,1'-methylene-bis-(naphthol-2) and the like.

The light stabilizers and the stabilizers can in each case be employed in an amount of 0.01 to 0.5 parts by weight based on 100 parts by weight of the monomer mixture.

The monomer mixtures can also be employed as coatings (dental varnishes) without an addition of fillers.

When used as tooth-filling compositions, the monomer mixtures obtained are generally additioned with fillers. Monomer mixtures having a viscosity in the range of 60 to 10,000 mPa.s are particularly advantageous to allow a high degree of filling to be achieved.

It is preferred to admix inorganic fillers to the (meth-)acrylic acid derivatives according to the invention. Examples which may be mentioned are rock crystal, cristobalite, quartz glass, highly-disperse silica, alumina and glass ceramics, for example zirconium-containing glass ceramics (German Offenlegungsschrift 23,740,501). The inorganic fillers are pretreated to improve bonding with the polymer matrix of the polymethacrylates, preferably using an adhesion promoter. Adhesion promotion can be achieved for example by treatment with organosilicon compounds (Progress in Organic Coatings 11, 297–308 (1983)). 3-Methacryloyloxypropyl-trimethoxysilane is preferably employed. In general, the fillers for the tooth-filling compositions according to the invention have an average particle diameter of 0.01 to 100 µm, preferably 0.03 to 50 µm, particularly preferably 0.03 to 5 µm. The concomitant use of a plurality of fillers which differ with regard to their mean particle diameter and/or silane content, can also be advantageous.

In general, the amount of filler in the tooth-filling composition is 5 to 85% by weight, preferably 50 to 80% by weight.

To prepare the tooth-filling compositions, the components are mixed using conventional kneading machines.

The amount of (meth) acrylates according to the invention in the tooth-filling compositions is, in general, 10 to 70% by weight based on the filling composition.

Tooth-filling materials which contain the monomers according to the invention show a low degree of shrinkage upon polymerization and give materials having a good mechanical strength, in particular good hardness and outstanding resistance to wear, and, moreover, their absorption is low.

EXAMPLES

Example 1 (Preparation of monomer 1)

178.5 g of bis(4-hydroxyphenyl)-3,3,5-trimethylcyclohexane, 122 g of triethylamine and 0.30 g of 2,6-di-tert-butyl- 4-methyl-phenol are dissolved in 1000 ml of methyl tert-butyl ether. 120.2 g of methacryloyl chloride are added dropwise to this solution at −5° C. in the course of 30 minutes. The solid which has formed is filtered off, the etheric solution is washed 3 times using 1000 ml of de-ionized water, dried over sodium sulphate and evaporated in vacuo at 35° C. 243 g of a colourless, crystalline solid are obtained (melting point: 119° C.).

Example 2 (Preparation of monomer 3)

Step 1, ethoxylation 1162.5 g of bis(4-hydroxyphenyl)-3,3,5-trimethylcyclohexane and 16.8 g of potassium hydroxide in 1575 g of deionized water are introduced into a VA stainless-steel autoclave at an $N_2$ pressure of 10 bar, and 924 g of ethylene oxide are added at 60° C. in the course of 10 hours. The mixture is then heated for 2 hours at 100° C. After cooling, 2 l of chloroform are added to the reaction mixture. A mixture of two phases results. The organic phase is separated off and washed seven times until neutral using 1000 ml of de-ionized water, dried over sodium sulphate and evaporated in vacuo at 100° C. 1372 g of a colourless, vitreously brittle solid are obtained.

Step 2, esterification 200.6 g of the ethoxylation product, 111.2 g of triethylamine and 0.30 g of 2,6-di-tert-butyl-4-methylphenol are dissolved in 1000 ml of dichloromethane. 104.5 g of methacryloyl chloride are added dropwise to this solution at −20° to −10° C. in the course of 30 minutes. When the addition has ended, the mixture is stirred for 1 hour at room temperature. The solid formed is filtered off, the etheric solution is washed 3 times using 1000 ml of deionized water, dried over sodium sulphate and evaporated in vacuo at 35° C. 241 g of a colourless solid are obtained (melting point: 91° C.).

Example 3 (Preparation of monomer 4)

Example 2 was repeated, but 90.5 g of acryloyl chloride were employed instead of 104.5 g of methacryloyl chloride. 219 g of colourless, viscous liquid are obtained.

Example 4 (Preparation of monomer 5)

Step 1, propoxylation 1162.5 g of bis(4-hydroxyphenyl)-3,3,5-trimethylcyclohexane and 16.8 g of potassium hydroxide in 1575 g of deionized water are introduced into a stainless-steel autoclave, this is purged using nitrogen, and 609 g of propylene oxide are added at 60° C. in the course of 3.5 hours. The mixture is then heated for 2 hours at 100° C. After cooling, 2 l of chloroform are added to the reaction mixture. A mixture of two phases results. The organic phase is separated off and washed seven times until neutral, using 1000 ml of de-ionized water, dried over sodium sulphate and evaporated in vacuo at 50° to 120° C. 1239 g of a colourless, vitreously brittle solid are obtained.

Step 2, esterification 206 g of the propoxylation product, 111.2 g of triethylamine and 0.30 g of 2,6-di-tert-butyl-4-methylphenol are dissolved in 1000 ml of dichloromethane. 104.5 g of (meth-)acryloyl chloride are added dropwise to this solution at −20° to −10° C. in the course of 30 minutes. When the addition has ended, the mixture is stirred for 1 hour at room temperature. The solid which has formed is filtered off, and the etheric solution is washed 3 times using in each case 500 ml of de-ionized water, dried over sodium sulphate and evaporated in vacuo at 35° C. 245 g of a slightly coloured, clear, viscous liquid are obtained.

We claim:

1. Dental articles comprising polymers obtained from monomers of the formula (IIIb)

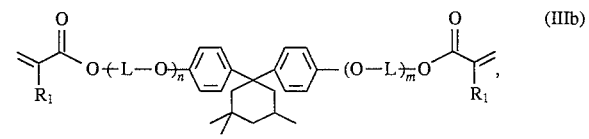

in which $R_1$ represents hydrogen or methyl,

L represents a $C_2$- to $C_6$-alkylene radical which can be substituted by alkyl, hydroxyl or halogen, and n and m independently of one another denote an integer from 1 to 4.

2. Dental articles according to claim 1, in which $R_1$ represents hydrogen or methyl, L represents a $C_2$- to $C_3$-alkylene radical which can be substituted by alkyl, hydroxyl or halogen, and n and m independently of one another denote 1 or 2.

3. Artificial teeth according to claim 1.

4. A dental filling composition comprising polymers obtained from monomers of the formula (IIIb)

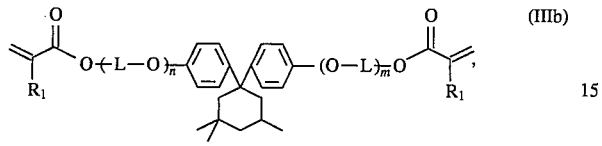

in which $R_1$ represents hydrogen or methyl,

L represents a $C_2$- to $C_6$-alkenylene radical which can be substituted by alkyl, hydroxyl or halogen, and n and m independently of one another denote an integer from 1 to 4, the composition comprising particles of the polymer 0.1 to 100 μm.

* * * * *